(12) United States Patent
Walsh et al.

(10) Patent No.: US 7,517,852 B2
(45) Date of Patent: Apr. 14, 2009

(54) COMPOSITIONS AND METHODS FOR TREATING BACTERIA

(75) Inventors: Scott Michael Walsh, White Plains, NY (US); Mary Catherine Pittaway, White Plains, NY (US); James J. Mond, Silver Springs, MD (US)

(73) Assignee: Biosynexus Incorporated, Gaithersburg, MD (US)

( * ) Notice: Subject to any disclaimer, the term of this patent is extended or adjusted under 35 U.S.C. 154(b) by 0 days.

(21) Appl. No.: 11/494,887

(22) Filed: Jul. 28, 2006

(65) Prior Publication Data

US 2007/0060506 A1   Mar. 15, 2007

Related U.S. Application Data

(60) Provisional application No. 60/779,034, filed on Mar. 3, 2006, provisional application No. 60/725,193, filed on Oct. 11, 2005, provisional application No. 60/703,010, filed on Jul. 28, 2005.

(51) Int. Cl.
*A61K 38/16* (2006.01)
(52) U.S. Cl. .......................................... 514/9
(58) Field of Classification Search ........................ None
See application file for complete search history.

(56) References Cited

U.S. PATENT DOCUMENTS

| 5,710,124 | A | | 1/1998 | Peel et al. |
|---|---|---|---|---|
| 5,753,614 | A | | 5/1998 | Blackburn et al. |
| 5,866,539 | A | * | 2/1999 | Blackburn et al. ............. 514/9 |
| 6,013,657 | A | * | 1/2000 | Lavon et al. ................ 514/330 |
| 2004/0192581 | A1 | | 9/2004 | Walsh et al. |

OTHER PUBLICATIONS

Bertino "Intranasal mupirocin for outbreaks of methicillin-resistant *Staphylococcus aureus*." Am. J. Health Syst. Pharm., 1997, 54, 2185-91.*
Mantovani et al. "Nisin Resistance of *Streptococcus bovis*," Appl. Environ. Microbiol., 2001; 67, 808-13.*
Johnson, "Antibiotic resistance among clinically important Gram-positive bacteria in the UK," Hospt. Infect., 1998, 40, 17-26.*
Baquero et al. "Antibiotic-selective environments," Clin. Infect. Dis., 1998, 27, S5-11, abstract only.*
Rode et al. "Efficacy of mupirocin in methicillin-resistant *Staphylococcus aureus* burn wound infection." Antimicrob. Agents Chemother., 1990, 33, 1358-61.*
Kluytmans et al. Reduction of Surgical-Site Infections in Cardiothoracic Surgery by Elimination of Nasal Carriage of *Staphylococcus aureus*. Infect. Cont. Hosp. Epidem. Nov. 1996, vol. 17, No. 12, pp. 780-785.

* cited by examiner

*Primary Examiner*—Cecilia Tsang
*Assistant Examiner*—Christina Marchetti Bradley
(74) *Attorney, Agent, or Firm*—Casimir Jones S.C.

(57) ABSTRACT

The present invention relates to the field of bacteriology. In particular, the present invention provides compositions (e.g., comprising a lantibiotic and mupirocin or gentamicin) and methods of treating (e.g., killing or inhibiting growth of) bacteria. For example, the present invention provides pharmaceutical compounds (e.g., comprising a lantibiotic and mupirocin or gentamicin) and methods of using the same in research, therapeutic and drug screening applications.

19 Claims, 14 Drawing Sheets

FIGURE 5

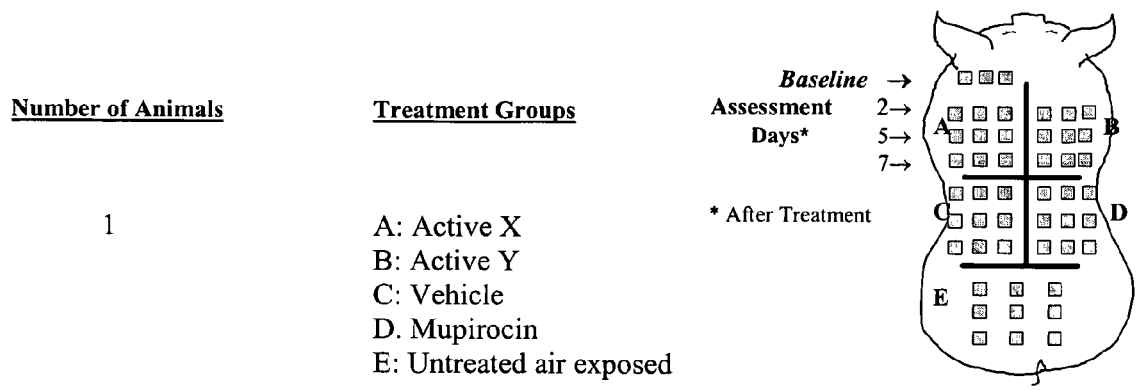

| Number of Animals | Treatment Groups |
|---|---|
| 1 | A: Active X<br>B: Active Y<br>C: Vehicle<br>D. Mupirocin<br>E: Untreated air exposed |

Day 0 = Wounding & Inoculation
Day 1 = 24 hours after inoculation
Day 2 = 48 hour biofilm (Day of Initial Treatment)
Day 3 = 2$^{nd}$ day of treatment
Day 4 = First Assessment Time (48 hours or Day 2 after initial treatment) – 3$^{rd}$ day of treatment
Day 5 = 4$^{th}$ day of treatment
Day 6 = 5$^{th}$ day of treatment
Day 7 = Second Assessment Time (168 hours or Day 5 after initial treatment) – 6$^{th}$ day of treatment
Day 8 = 7$^{th}$ day of treatment
Day 9 = Last Assessment Time (216 hours or Day 7 after initial treatment).

FIGURE 10
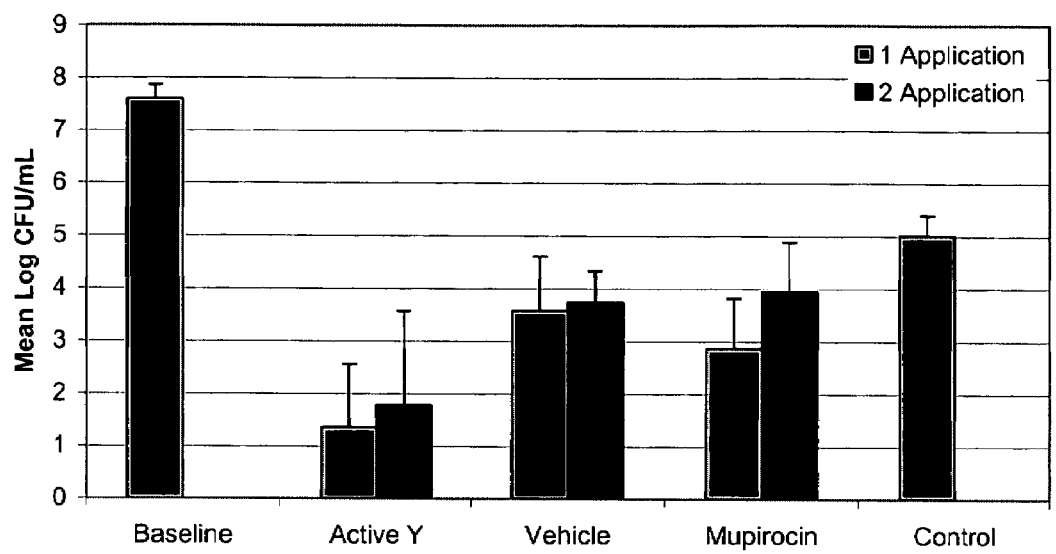
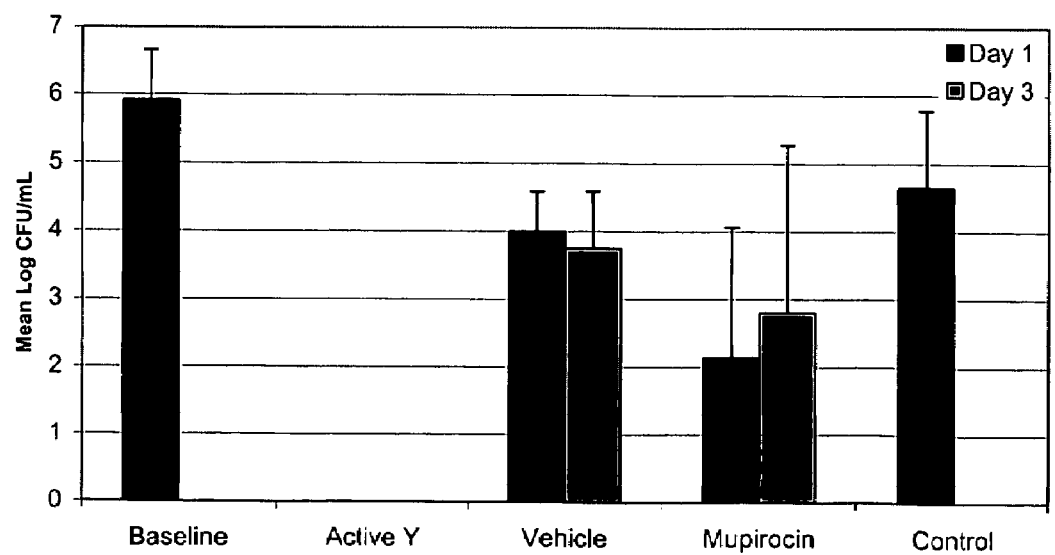

FIGURE 11

Gentamicin and Nisin

| | 0 | 0.03125 | 0.0625 | 0.125 | 0.25 | 0.5 | 1 | 2 | 4 | 8 | 16 | 32 | Gentamicin (ug/mL) |
|---|---|---|---|---|---|---|---|---|---|---|---|---|---|
| 0 | 0.659 | 0.684 | 0.676 | 0.69 | 0.69 | 0.645 | 0.518 | 0.041 | 0.032 | 0.032 | 0.031 | 0.032 | |
| 0.03125 | 0.684 | 0.7 | 0.682 | 0.681 | 0.685 | 0.658 | 0.531 | 0.034 | 0.032 | 0.033 | 0.034 | 0.032 | |
| 0.0625 | 0.682 | 0.683 | 0.685 | 0.676 | 0.677 | 0.645 | 0.548 | 0.034 | 0.034 | 0.033 | 0.033 | 0.032 | |
| 0.125 | 0.634 | 0.658 | 0.648 | 0.652 | 0.648 | 0.62 | 0.522 | 0.032 | 0.031 | 0.033 | 0.034 | 0.033 | |
| 0.25 | 0.236 | 0.232 | 0.257 | 0.295 | 0.245 | 0.234 | 0.331 | 0.034 | 0.032 | 0.032 | 0.034 | 0.032 | |
| 0.5 | 0.098 | 0.034 | 0.033 | 0.033 | 0.034 | 0.065 | 0.034 | 0.034 | 0.033 | 0.035 | 0.033 | 0.034 | |
| 1 | 0.033 | 0.033 | 0.033 | 0.036 | 0.033 | 0.033 | 0.032 | 0.034 | 0.034 | 0.034 | 0.035 | 0.034 | |
| 2 | 0.03 | 0.035 | 0.033 | 0.034 | 0.034 | 0.034 | 0.033 | 0.035 | 0.031 | 0.033 | 0.035 | 0.03 | |
| Nisin (ug/mL) | | | | | | | | | | | | | |

Neomycin and Nisin

| | 0 | 0.03125 | 0.0625 | 0.125 | 0.25 | 0.5 | 1 | 2 | 4 | 8 | 16 | 32 | Neomycin (ug/mL) |
|---|---|---|---|---|---|---|---|---|---|---|---|---|---|
| 0 | 0.768 | 0.685 | 0.65 | 0.645 | 0.716 | 0.692 | 0.65 | 0.467 | 0.032 | 0.032 | 0.03 | 0.032 | |
| 0.03125 | 0.703 | 0.709 | 0.691 | 0.685 | 0.71 | 0.701 | 0.657 | 0.457 | 0.032 | 0.034 | 0.033 | 0.035 | |
| 0.0625 | 0.708 | 0.702 | 0.703 | 0.696 | 0.696 | 0.681 | 0.655 | 0.446 | 0.034 | 0.032 | 0.033 | 0.032 | |
| 0.125 | 0.667 | 0.672 | 0.659 | 0.654 | 0.659 | 0.655 | 0.619 | 0.389 | 0.035 | 0.034 | 0.034 | 0.032 | |
| 0.25 | 0.332 | 0.304 | 0.285 | 0.256 | 0.304 | 0.322 | 0.386 | 0.178 | 0.033 | 0.032 | 0.034 | 0.032 | |
| 0.5 | 0.035 | 0.034 | 0.034 | 0.034 | 0.033 | 0.034 | 0.033 | 0.036 | 0.034 | 0.034 | 0.033 | 0.035 | |
| 1 | 0.034 | 0.034 | 0.034 | 0.033 | 0.033 | 0.035 | 0.035 | 0.034 | 0.034 | 0.034 | 0.034 | 0.033 | |
| 2 | 0.032 | 0.036 | 0.033 | 0.036 | 0.032 | 0.033 | 0.035 | 0.037 | 0.031 | 0.033 | 0.035 | 0.033 | |
| Nisin (ug/mL) | | | | | | | | | | | | | |

Mupirocin and Nisin

| | 0 | 0.001 | 0.001953 | 0.003906 | 0.007813 | 0.015625 | 0.03125 | 0.0625 | 0.125 | 0.25 | 0.5 | 1 | Mupirocin (ug/mL) |
|---|---|---|---|---|---|---|---|---|---|---|---|---|---|
| 0 | 0.632 | 0.677 | 0.703 | 0.696 | 0.553 | 0.156 | 0.037 | 0.034 | 0.033 | 0.033 | 0.03 | 0.031 | |
| 0.03125 | 0.66 | 0.71 | 0.701 | 0.687 | 0.56 | 0.153 | 0.034 | 0.031 | 0.03 | 0.03 | 0.031 | 0.028 | |
| 0.0625 | 0.667 | 0.692 | 0.686 | 0.685 | 0.565 | 0.156 | 0.039 | 0.03 | 0.03 | 0.029 | 0.03 | 0.029 | |
| 0.125 | 0.63 | 0.643 | 0.647 | 0.634 | 0.527 | 0.142 | 0.035 | 0.029 | 0.028 | 0.028 | 0.029 | 0.028 | |
| 0.25 | 0.255 | 0.481 | 0.538 | 0.384 | 0.412 | 0.119 | 0.033 | 0.028 | 0.03 | 0.028 | 0.029 | 0.03 | |
| 0.5 | 0.03 | 0.139 | 0.245 | 0.074 | 0.084 | 0.096 | 0.034 | 0.028 | 0.029 | 0.03 | 0.029 | 0.031 | |
| 1 | 0.03 | 0.029 | 0.36 | 0.028 | 0.029 | 0.041 | 0.03 | 0.031 | 0.029 | 0.028 | 0.029 | 0.029 | |
| 2 | 0.028 | 0.03 | 0.03 | 0.03 | 0.028 | 0.028 | 0.028 | 0.028 | 0.026 | 0.029 | 0.03 | 0.028 | |
| Nisin | | | | | | | | | | | | | |

FIGURE 14

| Treatment | Av. Count | Treatment | Av. Count | Treatment | Av. Count |
|---|---|---|---|---|---|
| Active X | 2.29 ± 2.0 | Active X | 0.77 ± 1.3 | Active X | 1.05 ± 1.8 |
| Active Y | 0 | Active Y | 0 | Active Y | 0 |
| Vehicle | 6.58 ± 0.4 | Vehicle | 1.5 ± 1.3 | Vehicle | 1.77 ± 1.57 |
| Mupirocin | 4.96 ± 0.8 | Mupirocin | 0.77 ± 1.3 | Mupirocin | 1.63 ± 1.42 |
| Control | 6.9 ± 0.9 | Control | 4.57 ± 1.2 | Control | 3.73 ± 1.70 |

COMPOSITIONS AND METHODS FOR TREATING BACTERIA

The present invention claims priority to U.S. Provisional Patent Application Nos. 60/703,010 filed Jul. 28, 2005; 60/725,193, filed Oct. 11, 2005; and 60/779,034, filed Mar. 3, 2006, each of which is hereby incorporated by reference in its entirety.

FIELD OF THE INVENTION

The present invention relates to the field of bacteriology. In particular, the present invention provides compositions (e.g., comprising a lantibiotic and mupirocin and/or gentamicin) and methods of treating (e.g., killing or inhibiting growth of) bacteria. For example, the present invention provides pharmaceutical compounds (e.g., comprising a lantibiotic and mupirocin and/or gentamicin) and methods of using the same in research, therapeutic and drug screening applications.

BACKGROUND OF THE INVENTION

As the use of conventional pharmaceutical antibiotics has increased for medical, veterinary and agricultural purposes, there has been a concurrent emergence of antibiotic-resistant strains of pathogenic bacteria.

The emergence of single- or multi-drug resistant bacteria can result from a gene mobilization that responds to selective pressures associated with antibiotic use. Over the last several decades, the increasingly frequent usage of antibiotics has acted in concert with spontaneous mutations arising in the bacterial gene pool to produce different strains of bacteria not susceptible to current antibacterial treatments. This repertoire of antibiotic resistant genes can be utilized by previously sensitive strains that have access to these genes (e.g., via conjugative transfer of plasmids or transposons). As a result, single- and multi-drug resistance genes are commonly found in a large variety of bacterial plasmids and conjugative transposons.

Gram-positive bacteria are a major cause of nosocomial infection. The most common pathogenic isolates in hospitals include *Enterococcus* spp., *Staphylococcus aureus, coagulase-negative staphylococci*, and *Streptococcus pneumoniae* (See, e.g., Principles and Practice of Infectious Diseases, 4th ed. Mandell G L, Bennett J E, Dolin R, ed. Churchill Livingstone, New York 1995), many strains of which are resistant to one or more antibiotics. *Enterococcus* spp. are part of the normal gut flora in humans. Of the more than seventeen enterococcal species, only *E. faecalis* and *E. faecium* commonly colonize and infect humans in detectable numbers (*E. faecalis* is isolated from approximately 80% of human infections, and *E. faecium* from most of the rest).

Vancomycin-resistant *enterococcus* (VRE) spp. are becoming increasingly common in hospital settings. In the first half of 1999, 25.9% of *entercoccal* isolates from Intensive Care Units were vancomycin-resistant; an increase from 16.6% in 1996 and from 0.4% in 1989. VRE are also commonly resistant to many other commercial antibiotics, including beta-lactams and aminoglycosides. Thus, patients who are immunocompromised or those having a prolonged hospital stay are at increased risk for acquiring a VRE infection.

The problem of antibiotic resistance is not unique to *Enterococcus* spp. Strains of many other potentially pathogenic Gram-positive bacteria displaying antibiotic resistance have been isolated including methicillin-resistant *Staphylococcus aureus* (MRSA), vancomycin-resistant *Staphylococcus aureus* (VRSA), glycopeptide intermediate-susceptible *Staphylococcus aureus* (GISA), vancomycin-resistant NRSA (VR-MRSA) and penicillin-resistant *Streptococcus pneumoniae* (PRSP). Like VRE, therapeutic options for treating infections by these organisms are limited.

Resistance transfer is another complicating factor in the management of antibiotic-resistant infections. Vancomycin resistance can transfer from VRE to other Gram-positive bacteria, including *S. aureus*, in vitro. Thus, the presence of resistant bacteria (e.g., VRE) in a hospital poses not just the risk of infection but also the continued evolution of resistant organisms (e.g., creating more virulent organisms such as VR-MRSA).

A need exists to develop alternative strategies of antibacterial treatment. For example, there exists a need for new compositions and methods of treating or preventing bacterial infection (e.g., bacteremia) caused by strains of bacteria unsusceptible to current forms of antibacterial treatments (e.g., Gram-positive bacteria such as MRSA and VRE).

SUMMARY OF THE INVENTION

The present invention relates to the field of bacteriology. In particular, the present invention provides compositions (e.g., comprising a lantibiotic and mupirocin and/or gentamicin) and methods of treating (e.g., killing or inhibiting growth of) bacteria. For example, the present invention provides pharmaceutical compounds (e.g., comprising a lantibiotic and mupirocin and/or gentamicin) and methods of using the same in research, therapeutic and drug screening applications.

Accordingly, in some embodiments, the present invention provides compositions and methods for the treatment of bacteria (e.g., bacterial infection). In some preferred embodiments, the present invention provides a combinatorial treatment for bacteria (e.g., a treatment that inhibits growth of and/or that kills bacteria). For example, in some embodiments, the present invention provides a composition comprising an anti-infective peptide (i.e., a peptide that inhibits growth or that is capable of killing bacteria (e.g., Gram positive bacteria)) and other type of anti-infective pharmaceutical or compound (e.g., non peptide anti-infective). In some embodiments, the anti-infective peptide is a cationic peptide. In some embodiments, the anti-infective peptide is a defensin. In some embodiments, the anti-infective peptide is a lantibiotic (e.g., nisin). In some embodiments, the second anti-infective agent is a small molecule antibiotic. In some embodiments, the second anti-infective agent is an antibiotic that alters bacterial metabolism (e.g., an antibiotic that interferes with cellular metabolism and/or RNA synthesis and/or protein synthesis). In some embodiments, the second anti-infective agent is an amino glycoside (e.g., gentimycin). In some embodiments, the second anti-infective agent is mupirocin. Although an understanding of the mechanism is not necessary to practice the present invention and the present invention is not limited to any particular mechanism of action, it is contemplated that a composition comprising an anti-infective peptide is capable of generating pores in bacteria thereby enhancing the entry of compounds (e.g., small molecule antibiotic or metabolism antibiotic) into bacteria. Although an understanding of the mechanism is not necessary to practice the present invention and the present invention is not limited to any particular mechanism of action, it is contemplated that the compositions of the present invention may stimulate (e.g., when in contact with the skin) a host defense response (e.g., an innate immune response) thereby decreasing the likelihood of or reducing bacterial infection.

In some embodiments, the present invention provides a topical pharmaceutical formulation comprising a lantibiotic and mupirocin. In some embodiments, the lantibiotic is nisin. However, the present invention is not limited by the type of lantibiotic utilized. Indeed, a number of lantibiotics may be used including, but not limited to, subtilin, epidermin, gallidermin, pep 5, cinnamycin, duramycin and ancovenin. In some embodiments, the pharmaceutical formulation is a cream. In some embodiments, the pharmaceutical formulation is a spray. In some embodiments, the pharmaceutical formulation is a gel or other type of formulation useful for administration of the lantibiotic and mupirocin. In some embodiments, the pharmaceutical formulation comprises polyethylene glycol. In some embodiments, the pharmaceutical formulation is prepared for controlled time release.

The present invention also provides a method of altering growth of bacteria comprising administrating to the bacteria a composition comprising a lantibiotic and mupirocin. In some embodiments, altering growth of bacteria comprises killing the bacteria. In some embodiments, altering growth of bacteria comprises inhibiting growth of the bacteria. In some embodiments, altering growth of bacteria comprises a 3 log or greater reduction of bacterial cell presence. In some embodiments, the lantibiotic is nisin. In some embodiments, the bacteria are pathogenic bacteria. In some embodiments, the bacteria are from the genus Staphylococci. In some embodiments, the bacteria are Staphylococcus aureus. In some embodiments, the bacteria are Staphylococcus epidermidis. In some embodiments, the Staphylococci are antibiotic resistant. For example, in some embodiments, the Staphylococcus aureus are methicillin resistant or vancomycin resistant. In some embodiments, the composition is a topical pharmaceutical formulation.

The present invention also provides a method for treating or preventing infection comprising exposing a surface of a subject to a topical pharmaceutical formulation comprising a lantibiotic and mupirocin. In some embodiments, exposing a surface of a subject to a topical pharmaceutical formulation comprising a lantibiotic and mupirocin treats or prevents growth of Staphylococcus aureus on the surface of the subject. The present invention is not limited by the type of surface treated. Indeed, a variety of surfaces may be treated including, but not limited to, skin surfaces (e.g., epidermis or sub-epidermal layers), wounds and cuts (e.g., superficial wounds, partial thickness wounds and deep cuts), mucosal surfaces, etc). The present invention is not limited by the type of subject treated. Indeed, a variety of subjects may be treated including, but not limited to, humans, large and small mammals, rodents, fish, etc. In some embodiments, the topical formulation comprises a cream. In some embodiments, treating results in a 3 log or greater reduction in bacteria responsible for the infection. In some embodiments, treating results in a lack of detectable bacteria responsible for the infection. In some embodiments, the reduction occurs within three days of treating. In some embodiments, the reduction occurs with two days of treating. In some embodiments, the lantibiotic is nisin. In some embodiments, the lantibiotic is gallidermin.

DESCRIPTION OF THE DRAWINGS

FIG. 5 depicts the experimental design of using compositions and methods of the present invention to treat partial thickness wounds.

FIG. 10 shows the mean log (CFU/ml) of bacteria recovered after either a first or second treatment (MSSA) or after one and three days (MRSA) of treatment with the reagents indicated.

FIG. 11 shows the minimum inhibitory concentration (MIC) of treatment of S. aureus in vitro with nisin alone or nisin in combination with either mupirocin, neomycin or gentamicin.

FIG. 14 shows data representing the log colony forming units/mL determined from cultured wounds 2, 5 and 7 days post treatment with compositions of the present invention.

DEFINITIONS

Figure 1:
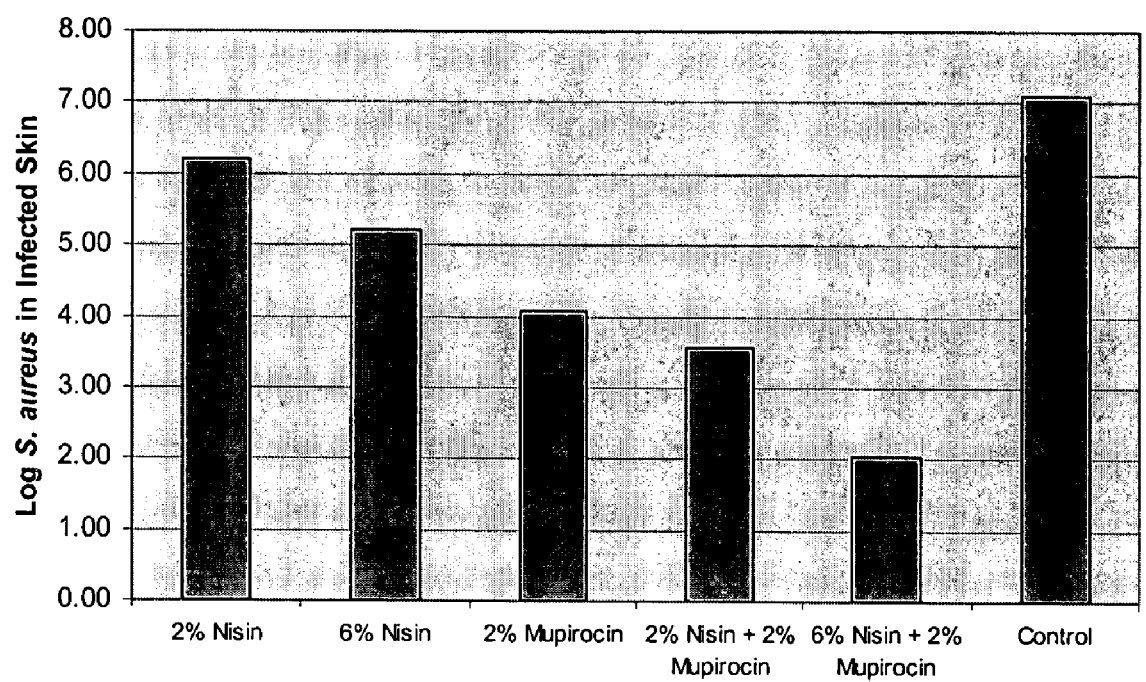
FIG. 1 shows the efficacy of nisin alone, mupirocin alone, and the combination of nisin and mupirocin on S. aureus infection in abraded mouse skin.

As used herein, the term "subject" refers to an individual (e.g., human, animal, or other organism) to be treated by the methods or compositions of the present invention. Subjects include, but are not limited to, mammals (e.g., murines, simians, equines, bovines, porcines, canines, felines, and the like), and most preferably includes humans. In the context of the invention, the term "subject" generally refers to an individual who will receive or who has received treatment for a condition characterized by the presence of bacteria (e.g., pathogenic bacteria such as MRSA), or in anticipation of possible exposure to bacteria. As used herein, the terms "subject" and "patient" are used interchangeably, unless otherwise noted.

The term "diagnosed," as used herein, refers to the recognition of a disease (e.g., caused by the presence of pathogenic bacteria) by its signs and symptoms (e.g., resistance to conventional therapies), or genetic analysis, pathological analysis, histological analysis, and the like.

As used herein the term, "in vitro" refers to an artificial environment and to processes or reactions that occur within an artificial environment. In vitro environments include, but are not limited to, test tubes and cell cultures. The term "in vivo" refers to the natural environment (e.g., an animal or a cell) and to processes or reaction that occur within a natural environment.

As used herein, the terms "attenuate" and "attenuation" used in reference to a feature (e.g. growth) of a bacterial cell or a population of bacterial cells refers to a reduction, inhibition or elimination of that feature, or a reducing of the effect(s) of that feature.

As used herein, the term "effective amount" refers to the amount of a composition (e.g., a composition comprising mupirocin and nisin) sufficient to effect a beneficial or desired result (e.g., bacterial cell killing). An effective amount can be administered in one or more administrations, applications or dosages and is not intended to be limited to a particular formulation or administration route.

As used herein, the term "administration" refers to the act of giving a drug, prodrug, or other agent, or therapeutic treatment (e.g., a composition of the present invention) to a physiological system (e.g., a subject or in vivo, in vitro, or ex vivo cells, tissues, and organs). Exemplary routes of administration to the human body can be through the eyes (ophthalmic), mouth (oral), skin (transdermal), nose (nasal), lungs (inhalant), mucosal (e.g., oral mucosa or buccal), rectal, ear, by injection (e.g., intravenously, subcutaneously, intratumorally, intraperitoneally, etc.) and the like.

As used herein, the term "treating a surface" refers to the act of exposing a surface to one or more compositions of the present invention. Methods of treating a surface include, but are not limited to, spraying, misting, submerging, and coating. Surfaces include organic surfaces (e.g., food products, surfaces of animals, etc.) and inorganic surfaces (e.g., medical devices, countertops, clothing, etc.).

As used herein, the term "co-administration" refers to the administration of at least two agent(s) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s).

As used herein, the term "toxic" refers to any detrimental or harmful effects on a subject, a cell, or a tissue as compared to the same cell or tissue prior to the administration of the toxicant.

As used herein, the term "pharmaceutical composition" refers to the combination of an active agent (e.g., a composition comprising mupirocin and nisin) with a carrier, inert or active, making the composition especially suitable for diagnostic or therapeutic use in vitro, in vivo or ex vivo.

The terms "pharmaceutically acceptable" or "pharmacologically acceptable," as used herein, refer to compositions that do not substantially produce adverse reactions (e.g., toxic, allergic, or immunological reactions) when administered to a subject.

As used herein, the term "topically" refers to application of the compositions of the present invention to the surface of the skin or mucosal cells and tissues (e.g., alveolar, buccal, lingual, masticatory, or nasal mucosa, and other tissues and cells that line hollow organs or body cavities).

As used herein, the term "pharmaceutically acceptable carrier" refers to any of the standard pharmaceutical carriers including, but not limited to, phosphate buffered saline solution, water, emulsions (e.g., such as an oil/water or water/oil emulsions), and various types of wetting agents, any and all solvents, dispersion media, coatings, sodium lauryl sulfate, isotonic and absorption delaying agents, disintrigrants (e.g., potato starch or sodium starch glycolate), and the like. The compositions also may include stabilizers and preservatives. Examples of carriers, stabilizers, and adjuvants are described in the art (See e.g., Martin, Remington's Pharmaceutical Sciences, 15th Ed., Mack Publ. Co., Easton, Pa. (1975), incorporated herein by reference).

As used herein, the term "medical devices" includes any material or device that is used on, in, or through a subject's or patient's body, for example, in the course of medical treatment (e.g., for a disease or injury). Medical devices include, but are not limited to, such items as medical implants, wound care devices, drug delivery devices, and body cavity and personal protection devices. The medical implants include, but are not limited to, urinary catheters, intravascular catheters, dialysis shunts, wound drain tubes, skin sutures, vascular grafts, implantable meshes, intraocular devices, heart valves, and the like. Wound care devices include, but are not limited to, general wound dressings, biologic graft materials, tape closures and dressings, and surgical incise drapes. Drug delivery devices include, but are not limited to, needles, drug delivery skin patches, drug delivery mucosal patches and medical sponges. Body cavity and personal protection devices, include, but are not limited to, tampons, sponges, surgical and examination gloves, and toothbrushes. Birth control devices include, but are not limited to, intrauterine devices (IUDs), diaphragms, and condoms.

As used herein, the term "therapeutic agent" refers to a composition that decreases the infectivity, morbidity, or onset of mortality in a subject contacted by a pathogenic microorganism or that prevent infectivity, morbidity, or onset of mortality in a host contacted by a pathogenic microorganism. Therapeutic agents encompass agents used prophylactically (e.g., in the absence of a pathogen) in view of possible future exposure to a pathogen. Such agents may additionally comprise pharmaceutically acceptable compounds (e.g., adjuvants, excipients, stabilizers, diluents, and the like). In some embodiments, the therapeutic agents of the present invention are administered in the form of topical compositions, injectable compositions, ingestible compositions, and the like. When the route is topical, the form may be, for example, a solution, cream, ointment, salve or spray.

As used herein, the term "pathogen" refers a biological agent that causes a disease state (e.g., infection, sepsis, etc.) in a host. "Pathogens" include, but are not limited to, viruses, bacteria, archaea, fungi, protozoans, mycoplasma, prions, and parasitic organisms.

The terms "bacteria" and "bacterium" refer to all prokaryotic organisms, including those within all of the phyla in the Kingdom *Procaryotae*. It is intended that the term encompass all microorganisms considered to be bacteria including *Mycoplasma, Chlamydia, Actinomyces, Streptomyces*, and *Rickettsia*. All forms of bacteria are included within this definition including cocci, bacilli, spirochetes, spheroplasts, protoplasts, etc. Also included within this term are prokaryotic organisms that are Gram-negative or Gram-positive. "Gram-negative" and "Gram-positive" refer to staining patterns with the Gram-staining process, which is well known in the art. (See e.g., Finegold and Martin, Diagnostic Microbiology, 6th Ed., CV Mosby St. Louis, pp. 13-15 (1982)). "Gram-positive bacteria" are bacteria that retain the primary dye used in the Gram stain, causing the stained cells to generally appear dark blue to purple under the microscope. "Gram-negative bacteria" do not retain the primary dye used in the Gram stain, but are stained by the counterstain. Thus, Gram-negative bacteria generally appear red. In some embodiments, bacteria are continuously cultured. In some embodiments, bacteria are uncultured and existing in their natural environment (e.g., at the site of a wound or infection) or obtained from patient tissues (e.g., via a biopsy). Bacteria may exhibit pathological growth or proliferation. Examples of bacteria include, but are not limited to, bacterial cells of a genus of bacteria selected from the group comprising *Salmonella, Shigella, Escherichia, Enterobacter, Serratia, Proteus, Yersinia, Citrobacter, Edwardsiella, Providencia, Klebsiella, Hafnia, Ewingella, Kluyvera, Morganella, Planococcus, Stomatococcus, Micrococcus, Staphylococcus, Vibrio, Aeromonas, Plessiomonas, Haemophilus, Actinobacillus, Pasteurella, Mycoplasma, Ureaplasma, Rickettsia, Coxiella, Rochalimaea, Ehrlichia, Streptococcus, Enterococcus, Aerococcus, Gemella, Lactococcus, Leuconostoc, Pedicoccus, Bacillus, Corynebacterium, Arcanobacterium, Actinomyces, Rhodococcus, Listeria, Erysipelothrix, Gardnerella, Neisseria, Campylobacter, Arcobacter, Wolinella, Helicobacter, Achromobacter, Acinetobacter, Agrobacterium, Alcaligenes, Chryseomonas, Comamonas, Eikenella, Flavimonas, Flavobacterium, Moraxella, Oligella, Pseudomonas, Shewanella, Weeksella, Xanthomonas, Bordetella, Franciesella, Brucella, Legionella, Afipia, Bartonella, Calymmatobacterium, Cardiobacterium, Streptobacillus, Spirillum, Peptostreptococcus, Peptococcus, Sarcinia, Coprococcus, Ruminococcus, Propionibacterium, Mobiluncus, Bifidobacterium, Eubacterium, Lactobacillus, Rothia, Clostridium, Bacteroides, Porphyromonas, Prevotella, Fusobacterium, Bilophila, Leptotrichia, Wolinella, Acidaminococcus, Megasphaera, Veilonella, Norcardia, Actinomadura, Norcardiopsis, Streptomyces, Micropolysporas, Thermoactinomycetes, Mycobacterium, Treponema, Borrelia, Leptospira*, and *Chlamydiae*.

As used herein, the term "microorganism" refers to any species or type of microorganism, including but not limited to, bacteria, archaea, fungi, protozoans, mycoplasma, and parasitic organisms.

As used herein, the term "non-human animals" refers to all non-human animals including, but not limited to, vertebrates such as rodents, non-human primates, ovines, bovines, ruminants, lagomorphs, porcines, caprines, equines, canines, felines, aves, etc.

As used herein, the term "kit" refers to any delivery system for delivering materials. In the context of reaction materials (e.g., compositions comprising mupirocin and nisin), such delivery systems include systems that allow for the storage, transport, or delivery of reaction reagents and/or supporting materials (e.g., written instructions for using the materials, etc.) from one location to another. For example, kits include one or more enclosures (e.g., boxes) containing the relevant reaction reagents and/or supporting materials. As used herein, the term "fragmented kit" refers to delivery systems comprising two or more separate containers that each contain a subportion of the total kit components. The containers may be delivered to the intended recipient together or separately. For example, a first container may contain a composition comprising mupirocin and nisin for a particular use, while a second container contains a second agent (e.g., an antibiotic or spray applicator). Indeed, any delivery system comprising two or more separate containers that each contains a subportion of the total kit components are included in the term "fragmented kit." In contrast, a "combined kit" refers to a delivery system containing all of the components of a reaction materials needed for a particular use in a single container (e.g., in a single box housing each of the desired components). The term "kit" includes both fragmented and combined kits.

DETAILED DESCRIPTION OF THE INVENTION

*Staphylococci* are gram positive bacterial pathogens that cause a wide variety of diseases ranging from superficial abscesses (e.g., boils, styes, furuncles and other localized abscesses) to deeper infections (e.g., osteomyelitis, pneumonia, endocarditis, urinary tract infections, septic arthritis, meningitis, post-operative wound infections, septicemia and food poisoning). *S. aureus* is a major cause of hospital acquired (nosocomial) infection of surgical wounds and *S. epidermidis* causes infections associated with indwelling medical devices. (See, e.g., Silverstein et al., 1990; Patti et al., 1994; Dann et al., 1994.)

Multiple antibiotic resistance is increasingly common in *S. aureus* and *S. epidermidis*. Hospital strains of *Staphylococcus* are often resistant to many different antibiotics. *S epidermidis* nosocomial isolates are also often resistant to several antibiotics including methicillin. In addition, *S. aureus* expresses resistance to antiseptics and disinfectants, such as quaternary ammonium compounds, that may aid its survival in the hospital environment.

For serious hospital infections with multi-drug resistant *S. aureus*, vancomycin had existed as the only effective antibiotic. Vancomycin resistance is carried by conjugative plasmids that can be transferred to *S. aureus* in a laboratory setting (Noble et al., 1992) and has appeared naturally in enterococci (See, e.g., Arthur et al., 1993). However, the appearance of vancomycin resistant *S. aureus* has been reported (See, e.g., Lowry, 1998; Mathews et al., J Acquir Immune Defic Syndr. 2005 Oct. 1;40(2):155-160) in the U.S. and abroad. Vaccines have been developed targeting the organism or exotoxins it produces, but these approaches have met with little success (See, e.g., Mamo et al., 1994), underscoring the need to develop new methods to control *Staphylococcal* infections.

Similar to other gram positive bacteria, *S. aureus* causes disease chiefly through the production of virulence factors such as hemolysins, enterotoxins and toxic shock syndrome toxin, which facilitate the survival, multiplication and spread of the organism in infected tissue (See, e.g., Mekalanos, 1992). The synthesis of most virulence factors in *S. aureus* is controlled by the accessory global regulon (agr) locus, which is activated by secreted autoinducing peptides (AIPs) (See, e.g., Novick et al., 1993; Novick et al., 1995).

The presence of agr and regulation of virulence by RNAIII has been demonstrated in all strains of *S. aureus* tested to date as well as several other species of staphylococci including *S. epidermidis, S. lugdunesis, S. hemolyticus* (See, e.g., Vandenesch et al., 1993), and *S. warneri* (See, e.g., Tegmark et al., 1998).

*S. aureus* infection remains one of the most common nosocomial and community-acquired infections. With the continuing emergence of methicillin-resistant *S. aureus* (MRSA) and strains of *S. aureus* that are intermediately resistant to glycopeptides and the isolation of clinical strain of *S. aureus* that are fully vancomycin resistant, *S. aureus* is becoming an even more difficult health problem to address, particularly in settings such as hospitals and nursing homes.

Curreritly, BACTROBAN (2% mupirocin ointment; SmithKline Beecham, Bristol, Tenn.) is the most widely prescribed and effective antibacterial agent for treatment of *S. aureus* skin infections. Mupirocin is an antibacterial agent produced by fermentation using the organism *Pseudomonas fluorescens*. It is active against a wide range of gram-positive bacteria including most strains of *S. aureus*, including methicillin-resistant *S. aureus* (MRSA), most strains of *S. epidermidis, S. saprophyticus*, and *Streptococcus*. Mupirocin inhibits bacterial protein synthesis by reversibly and specifically binding to bacterial isoleucyl transfer-RNA synthetase. Due to this unique mode of action, mupirocin demonstrates no in vitro cross-resistance with other classes of anti-microbial agents. Although BACTROBAN (2% mupirocin) is a common treatment, a variety of compounds similar to mupirocin (e.g., derivatives and functional equivalents) are in use or in development and are known in the art.

Unfortunately, as with many antimicrobials, mupirocin resistance is emerging in *S. aureus* and coagulase-negative *Staphylococci*. Furthermore, this antibiotic does not routinely eliminate all infectious organisms in all patients.

Nisin is an antimicrobial substance produced by *Lactococcus lactis* belonging to the Lancefield serological group. It is a member of a group of similar substances referred to as lantibiotics, that include, but are not limited to, subtilin, epidermin, gallidermin, pep 5, cinnamycin, duramycin and ancovenin. Nisin is a peptide comprised of 34-amino acid residues and contains five ring structures cross-linked by thioether bridges that form lanthionine or β-methyllanthionine. Formulations of nisin are described in U.S. Pat. Nos. 5,135,910 and 5,753,614, herein incorporated by reference in their entireties. Variants of nisin are described in U.S. Pat. No. 6,448,034, herein incorporated by reference in its entirety. Additional lantibiotics similar to nisin are described in U.S. Pat. Nos. 5,594,103 and 5,928,146, herein incorporated by reference in their entireties.

Nisin has broad-spectrum activity against gram positive bacteria and some activity against gram negative bacteria. Nisin has been used as an antimicrobial food preservative and is generally accepted as safe. Blackburn et al. (See U.S. Pat. No. 5,866,539, hereby incorporated by reference in its entirety) generally describes use of nisin along with antibacterial agents to treat skin infections.

Despite impressive successes in controlling or eliminating bacterial infections by antibiotics, the widespread use of antibiotics both in human medicine and as a feed supplement in poultry and livestock production has led to drug resistance in many pathogenic bacteria. The emergence of pan-resistant strains of *Staphylococci* (e.g., strains that are unsusceptible to current forms of antibacterial treatment) makes the need to control *Staphylococcal* infection an important medical concern. Thus, it is desirable to provide new compositions and methods of treatment that display efficacy in reducing the incidence and severity of *Staphylococcal* infection. Specifically, there is a need for new treatments for resistant strains of bacteria, in particular, *S. aureus* strains that are resistant to mupirocin and other antibiotics. There is also a need for anti-infectives that have a broader range of activity against gram negative bacteria, and for more effective anti-infectives. Additionally, it would be beneficial for such treatments to be well tolerated by patients with minimal or no side effects.

Accordingly, the present invention provides compositions and methods for the treatment of bacteria (e.g., bacterial infection). In some preferred embodiments, the present invention provides a combinatorial treatment for bacteria (e.g., a treatment that inhibits growth of and/or that kills bacteria). For example, in some embodiments, the present invention provides a composition comprising an anti-infective peptide (i.e., a peptide that inhibits growth or that is capable of killing bacteria (e.g., Gram positive bacteria)) and other type of anti-infective pharmaceutical or compound (e.g., non peptide anti-infective). In some embodiments, the anti-infective peptide is a cationic peptide. In some embodiments, the anti-infective peptide is a defensin. In some embodiments, the anti-infective peptide is a lantibiotic (e.g., nisin). In some embodiments, the second anti-infective agent is a small molecule antibiotic. In some embodiments, the second anti-infective agent is an antibiotic that alters bacterial metabolism (e.g., an antibiotic that interferes with cellular metabolism and/or RNA synthesis and/or protein synthesis). In some embodiments, the second anti-infective agent is an amino glycoside (e.g., gentimycin). In some embodiments, the second anti-infective agent is mupirocin. Although an understanding of the mechanism is not necessary to practice the present invention and the present invention is not limited to any particular mechanism of action, it is contemplated that a composition comprising an anti-infective peptide is capable of generating pores in bacteria thereby enhancing the entry of compounds (e.g., small molecule antibiotic or metabolism antibiotic) into bacteria. Although an understanding of the mechanism is not necessary to practice the present invention and the present invention is not limited to any particular mechanism of action, it is contemplated that the compositions of the present invention may stimulate (e.g., when in contact with the skin) a host defense response (e.g., an innate immune response) thereby decreasing the likelihood of or reducing bacterial infection.

In other preferred embodiments, the present invention provides a composition comprising nisin and mupirocin. In some embodiments, a composition comprising nisin and mupirocin is administered to a subject under conditions such that bacteria (e.g., pathogenic bacteria) are killed. In some embodiments, a composition comprising nisin and mupirocin is administered to a subject under conditions such that bacteria (e.g., pathogenic bacteria) growth is prohibited and/or attenuated. In some embodiments, greater than 90% (e.g., greater than 95%, 98%, 99%, all detectable) of bacteria are killed. In some embodiments, there is greater than 2 log (e.g., greater than 3 log, 4 log, 5 log, or more) reduction in bacteria. In some embodiments, the reduction is observed in two days or less following initial treatment (e.g., less than 24 hours, less than 20 hours, 18 hours or less). In some embodiments, the reduction is observed in three days or less, four days or less, or five days or less.

The present invention demonstrates that a composition comprising a lantibiotic (e.g., nisin) and mupirocin is more efficacious (e.g., in some embodiments, provides an additive effect, and in other embodiments, provides a synergistic effect) at treating skin infections (e.g., killing bacteria or prohibiting bacterial growth (e.g., of subcutaneous skin infections or deep wound infections)) when compared to either agent alone (See Example 1). The specific efficacy of a composition comprising a lantibiotic (e.g., nisin) and mupirocin compared to a lantibiotic (e.g., nisin) plus other type of antibacterial agent was observed during the development of the present invention. For example, when nisin was combined with two other anti-bacterial agents separately (lysostaphin and bacitracin), no additive or synergistic effect was observed. Thus, in some embodiments, the present invention provides a composition comprising mupirocin and a lantibiotic (e.g., nisin).

A composition comprising mupirocin and a lantibiotic (e.g., nisin) of the present invention can be administered (e.g., to a subject (e.g., to the skin or other surface of a subject) or to bacteria (e.g., pathogenic bacteria (e.g., residing on or within the skin of a subject))) as a therapeutic or as a prophylactic to prevent bacterial infection. Thus, in some embodiments, the present invention provides a method of altering bacterial (e.g., pathogenic bacteria) growth comprising administering a composition comprising a lantibiotic (e.g., nisin) and mupirocin to the bacteria. In some embodiments, administration of a composition comprising a lantibiotic (e.g., nisin) and mupirocin to the bacteria kills the bacteria. In some embodiments, administration of a composition comprising a lantibiotic (e.g., nisin) and mupirocin to the bacteria inhibits growth of the bacteria. It is contemplated that a composition comprising mupirocin and a lantibiotic (e.g., nisin)

can be administered (e.g., to a subject or bacteria) via a number of delivery routes and/or mechanisms.

For example, the compositions of the present invention can be administered (e.g., to a subject (e.g., to a skin burn or wound surface)) by multiple methods, including, but not limited to, being suspended in a solution (e.g., colloidal solution) and applied to a surface (e.g., a surface comprising bacteria (e.g., pathogenic bacteria) or susceptible to bacterial invasion); being suspended in a solution and sprayed onto a surface using a spray applicator; being mixed with fibrin glue and applied (e.g., sprayed) onto a surface (e.g., skin burn or wound); being impregnated onto a wound dressing or bandage and applying the bandage to a surface (e.g., an infection or wound); being applied by a controlled-release mechanism; being impregnated on one or both sides of an acellular biological matrix that can then be placed on a surface (e.g., skin wound or burn) thereby protecting at both the wound and graft interfaces; being applied as a liposome; or being applied on a polymer.

While an understanding of the mechanism is not necessary to practice the present invention and while the present invention is not limited to any particular mechanism of action, it is contemplated that, in some embodiments, once administered (e.g., to a subject or to a site comprising bacteria (e.g., pathogenic bacteria (e.g., MRSA))), compositions (e.g., a topical pharmaceutical composition) comprising mupirocin and nisin come into contact with bacteria (e.g., pathogenic bacteria) thereby killing and/or preventing growth of the bacteria.

In some embodiments, compositions and methods of the present invention find application in the treatment of surfaces for the attenuation or growth inhibition of unwanted bacteria (e.g., pathogens). For example, surfaces that may be used in invasive treatments such as surgery, catheterization and the like may be treated to prevent infection of a subject by bacterial contaminants on the surface. It is contemplated that the methods and compositions of the present invention may be used to treat numerous surfaces, objects, materials and the like (e.g., medical or first aid equipment, nursery and kitchen equipment and surfaces) in order to control and/or prevent bacterial contamination thereon.

In some embodiments, a composition of the present invention may be impregnated into absorptive materials, such as sutures, bandages, and gauze, or coated onto the surface of solid phase materials, such as surgical staples, zippers and catheters to deliver the compositions to a site for the prevention of microbial infection. Other delivery systems of this type will be readily apparent to those skilled in the art.

Other uses for a composition comprising mupirocin and nisin of the invention are also contemplated. These include a variety of agricultural, horticultural, environmental and food processing applications. For example, in agriculture and horticulture, various plant pathogenic bacteria may be targeted in order to minimize plant disease. One example of a plant pathogen suitable for targeting is *Erwinia amylovora*, the causal agent of fire blight.

The compositions of the invention may be formulated for administration by any route, such as oral, topical or parenteral. The compositions may be in the form of tablets, capsules, powders, granules, lozenges, creams or liquid preparations, such as oral or sterile parenteral solutions or suspensions.

The topical formulations of the present invention may be presented as, for instance, ointments, creams or lotions, foams, eye ointments and eye or ear drops, impregnated dressings and aerosols, and may contain appropriate conventional additives such as preservatives, solvents to assist drug penetration, and emollients in ointments and creams.

The topical formulations may also include agents that enhance penetration of the active ingredients through the skin. Exemplary agents include a binary combination of N-(hydroxyethyl)pyrrolidone and a cell-envelope disordering compound, a sugar ester in combination with a sulfoxide or phosphine oxide, and sucrose monooleate, decyl methyl sulfoxide, and alcohol.

Other exemplary materials that increase skin penetration include surfactants or wetting agents including, but not limited to, polyoxyethylene sorbitan mono-oleoate (Polysorbate 80); sorbitan mono-oleate (Span 80); p-isooctyl polyoxyethylene-phenol polymer (Triton WR-1330); polyoxyethylene sorbitan tri-oleate (Tween 85); dioctyl sodium sulfosuccinate; and sodium sarcosinate (Sarcosyl NL-97); and other pharmaceutically acceptable surfactants.

In certain embodiments of the invention, the formulations may further comprise one or more alcohols, zinc-containing compounds, emollients, humectants, thickening and/or gelling agents, neutralizing agents, and surfactants. Water used in the formulations is preferably deionized water having a neutral pH. Additional additives in the topical formulations include, but are not limited to, silicone fluids, dyes, fragrances, pH adjusters, and vitamins.

The topical formulations may also contain compatible conventional carriers, such as cream or ointment bases and ethanol or oleyl alcohol for lotions. Such carriers may be present as from about 1% up to about 98% of the formulation. The ointment base can comprises one or more of petrolatum, mineral oil, ceresin, lanolin alcohol, panthenol, glycerin, bisabolol, cocoa butter and the like.

In some embodiments of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, preferably do not unduly interfere with the biological activities of the components of the compositions of the present invention. The formulations can be sterilized and, if desired, mixed with auxiliary agents (e.g., lubricants, preservatives, stabilizers, wetting agents, emulsifiers, salts for influencing osmotic pressure, buffers, colorings, flavorings and/or aromatic substances and the like) that do not deleteriously interact with mupirocin and nisin of the formulation.

In some embodiments, the invention provides a pharmaceutical composition containing (a) a composition comprising mupirocin and a lantibiotic (e.g., nisin); and (b) one or more other agents (e.g., an antibiotic). Examples of other types of antibiotics include, but are not limited to, almecillin, amdinocillin, amikacin, amoxicillin, amphomycin, amphotericin B, ampicillin, azacitidine, azaserine, azithromycin, azlocillin, aztreonam, bacampicillin, bacitracin, benzyl penicilloyl-polylysine, bleomycin, candicidin, capreomycin, carbenicillin, cefaclor, cefadroxil, cefamandole, cefazoline, cefdinir, cefepime, cefixime, cefmenoxime, cefmetazole, cefodizime, cefonicid, cefoperazone, ceforanide, cefotaxime, cefotetan, cefotiam, cefoxitin, cefpiramide, cefpodoxime, cefprozil, cefsulodin, ceftazidime, ceftibuten, ceftizoxime, ceftriaxone, cefuroxime, cephacetrile, cephalexin, cephaloglycin, cephaloridine, cephalothin, cephapirin, cephradine, chloramphenicol, chlortetracycline, cilastatin, cinnamycin, ciprofloxacin, clarithromycin, clavulanic acid, clindamycin, clioquinol, cloxacillin, colistimethate, colistin, cyclacillin, cycloserine, cyclosporine, cyclo-(Leu-Pro), dactinomycin, dalbavancin, dalfopristin, daptomycin, daunorubicin, demeclocycline, detorubicin, dicloxacillin, dihydrostreptomycin, dirithromycin, doxorubicin, doxycycline, epirubicin, erythromycin, eveminomycin, floxacillin, fosfomycin, fusidic acid, gemifloxacin, gentamycin, gramicidin, griseofulvin, hetacillin, idarubicin, imipenem, iseganan, ivermectin, kanamycin, laspartomycin, linezolid, linocomycin, loracarbef, magainin, meclocycline, meropenem, methacycline, methicillin, mezlocillin, minocycline, mitomycin, moenomycin, moxalactam, moxifloxacin, mycophenolic acid, nafcillin, natamycin, neomycin, netilmicin, niphimycin, nitrofurantoin, novobiocin, oleandomycin, oritavancin, oxacillin, oxytetracycline, paromomycin, penicillamine, penicillin G, penicillin V, phenethicillin, piperacillin, plicamycin, polymyxin B, pristinamycin, quinupristin, rifabutin, rifampin, rifamycin, rolitetracycline, sisomicin, spectrinomycin, streptomycin, streptozocin, sulbactam, sultamicillin, tacrolimus, tazobactam, teicoplanin, telithromycin, tetracycline, ticarcillin, tigecycline, tobramycin, troleandomycin, tunicamycin, tyrthricin, vancomycin, vidarabine, viomycin, virginiamycin, BMS-284,756, L-749,345, ER-35,786, S-4661, L-786, 392, MC-02479, Pep5, RP 59500, and TD-6424. In some embodiments, two or more combined agents (e.g., a composition comprising mupirocin and nisin and another antibiotic) may be used together or sequentially. In some embodiments, another antibiotic may comprise bacteriocins, type A lantibiotics, type B lantibiotics, liposidomycins, mureidomycins, alanoylcholines, quinolines, eveminomycins, glycylcyclines, carbapenems, cephalosporins, streptogramins, oxazolidonones, tetracyclines, cyclothialidines, bioxalomycins, cationic peptides, and/or protegrins. In some embodiments, the composition comprises lysostaphin.

The present invention also includes methods involving co-administration of compounds comprising mupirocin and a lantibiotic (e.g., nisin) with one or more additional active agents (e.g., an antibiotic, anti-oxidant, etc.). Indeed, it is a further aspect of this invention to provide methods for enhancing prior art therapies and/or pharmaceutical compositions by co-administering a composition comprising mupirocin and nisin of this invention. In co-administration procedures, the agents may be administered concurrently or sequentially. In one embodiment, the compounds described herein are administered prior to the other active agent(s). The pharmaceutical formulations and modes of administration may be any of those described herein. In addition, the two or more co-administered agents may each be administered using different modes or different formulations.

The additional agents to be co-administered, such as other antibiotics, can be any of the well-known agents in the art, including, but not limited to, those that are currently in clinical use.

Treatment of the various diseases and disorders described herein are often generally limited by the following two major factors: (1) the development of drug resistance and (2) the toxicity of known therapeutic agents. Some therapeutic agents have deleterious side effects, including non-specific toxicity.

The methods described herein address both these problems. Drug resistance, where increasing dosages are required to achieve therapeutic benefit, is overcome by co-administering the compounds comprising mupirocin and a lantibiotic (e.g., nisin) described herein with or without a known agent. In some embodiments, the compounds described herein sensitize target cells to known agents (and vice versa) and, accordingly, less of these agents are needed to achieve a therapeutic benefit.

The sensitizing function of the claimed compositions also addresses the problems associated with toxic effects of known therapeutics. In instances where the known agent is toxic, it is desirable to limit the dosages administered in all cases, and particularly in those cases where drug resistance has increased the requisite dosage. Thus, in some embodiments, when the claimed compounds are co-administered with the known agent, they reduce the dosage required which, in turn, reduces the deleterious effects. Further, because the claimed compounds are themselves both effective and non-toxic in moderate doses, co-administration of proportionally more of these compounds than known toxic therapeutics will achieve the desired effects while minimizing toxic effects.

In some embodiments, pharmaceutical preparations comprising compositions comprising mupirocin and nisin are formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of the compositions comprising mupirocin and a lantibiotic (e.g., nisin) calculated to produce the desired antibacterial (e.g., killing or growth attenuation of bacteria) effect in association with the selected pharmaceutical carrier. Procedures for determining the appropriate dosage unit are well known to those skilled in the art.

Dosage units may be proportionately increased or decreased based on the weight of the patient. Appropriate concentrations for achieving eradication of pathogenic bacteria in a target cell population or tissue may be determined by dosage concentration curve calculations, as known in the art.

In some embodiments, the composition comprises from 0.1 to 2000 µg/mL of lantibiotic (e.g., nisin) and 0.1 to 2000 µg/mL mupirocin (e.g., 1-1000 µg/mL, 1-500 µg/mL, 5-200 µg/mL etc.). In some embodiments, the composition is from 0.01 to 15% (e.g., 0.1-10%, 0.5-5%, 1-3%, 2%) by weight lantibiotic (e.g., nisin) and/or mupirocin. In some embodiments, the amount of lantibiotic (e.g., nisin) and/or mupirocin delivered to a subject is from 0.1 to 1000 mg/kg/day (e.g., 1 to 500 mg/kg/day, 5 to 250 mg/kg/day, 10-100 mg/kg/day, etc.). In some embodiments, the ratio of lantibiotic (e.g., nisin) concentration to mupirocin concentration is 10:1, 5:1, 3:1, 2:1, 1.5:1, 1:1, 1:1.5, 1:2, 1:3, 1:5, 1:10, etc.

It is contemplated that the compositions and methods of the present invention will find use in various settings, including research settings. For example, compositions and methods of the present invention also find use in studies of antibiotic resistance (e.g., via analysis of proteins and pharmaceuticals capable of altering antibiotic resistance) and in in vivo studies to observe susceptibility of bacterial cells to antibacterial treatments. Uses of the compositions and methods provided by the present invention encompass human and non-human subjects and samples from those subjects, and also encompass research applications using these subjects. Thus, it is not intended that the present invention be limited to any particular subject and/or application setting.

The compositions of the present invention find use where the nature of the infection present or to be avoided is known, as well as where the nature of the infection is unknown. For example, the present invention contemplates use of the compositions of the present invention in treatment of or prevention of infections associated with any topical application involving ailments of the skin, including, but not limited to, skin lesions, wounds, ulcers, bed sores, diaper rash, blisters, acne, psoriasis, and warts.

EXPERIMENTAL

The following examples are provided in order to demonstrate and further illustrate certain preferred embodiments and aspects of the present invention and are not to be construed as limiting the scope thereof.

Example 1

Compositions Comprising Mupirocin and Nisin Clear Mouse Skin Infection

Materials: Lysostaphin was made by Biosynexus, Inc. and Nisin (AMBICIN N) was obtained from AMBI, Inc. Mupirocin (BACTROBAN Ointment), bacitracin (Sigma), and Bacitracin Ointment (G&W Laboratories Inc) were all obtained commercially. Polyethylene glycol (PEG) 400 and PEG 3350 were purchased from Spectrum Chemicals.

Mouse Skin Infection Model: An overnight culture of S. aureus grown in tryptic soy broth (SA8; range from 1 to $6 \times 10^9$ CFUs/mL) was centrifuged at 4000×g for 10 minutes and resuspended in an equal volume of phosphate buffered saline (PBS). The bacteria were diluted to a percent transmittance of 40 (Spectronic 20D+) and diluted a subsequent 1:1000 in PBS for a final bacteria concentration of about $3 \times 10^5$. SKH1 (hrhr) hairless mice (Charles River) were sedated with 0.2 mL of ketamine (80 mg/kg) and xylazine (32 mg/kg) delivered intraperitoneally. The upper back of the mice were scrubbed with a 70% alcohol wipe and allowed to dry. Fine abrasions were made on the backs of the mice between the shoulders using 150 grit sandpaper. Bacteria were swabbed over the abraded area with a sterile, cotton-tipped applicator until the area was saturated with the solution.

Topical Ointment: 74 g of PEG 400 and 24 g of PEG 3350 were added to a 250 mL glass beaker and heated until all of the PEG 3350 was melted. The solution was stirred well and allowed to cool to room temperature, which resulted in a smooth, opaque ointment. Powdered nisin and bacitracin were added to the ointment on a w/w basis and stirred until homogenously mixed. For formulations containing mupirocin, 1 g of Bactroban Ointment was weighed into a container and powdered nisin added to 2% or 6% (w/w) and mixed well. Lysostaphin was first dissolved to a concentration of about 150 mg/mL in DI water before mixing into the ointment to give a final concentration of 2% (w/w).

Treatment of Infected Skin with Topical Ointment: Treatments aimed to eradicate S. aureus skin infections in the mouse model were started on the morning after infection (Day 1). About 0.1 g of the topical ointments containing nisin (0, 2, or 6% w/w), mupirocin (0 or 2%), bacitracin (0 or 500U), and lysostaphin (0 or 2% w/w) were swabbed over the infected area 3 times a day on Days 1 and 2 using a sterile, polyester-tipped applicator. The mice were sacrificed by $CO_2$ asphyxiation on the morning of Day 3 and a 0.5-$cm^2$ patch of skin around the infected area was excised. The skin sample was disected and placed into a test tube containing 1 mL of 5 mg/mL proteinase K, 20 mg/mL esterase, and 20 mg/mL activated charcoal in PBS to neutralize the activity of the antibacterial agents. Bacteria were dislodged from the skin sample by sonication: 2 minute treatments per sample with alternating 5 seconds at 3 W and 5 seconds at 0 W in a Virsonic 600 with microtip (VirTis). After mixing by vortex, 50 µL of each sample was streaked onto blood agar plates, incubated at 37° C. overnight, and the colonies were counted and compared. to untreated controls.

Figure 2:
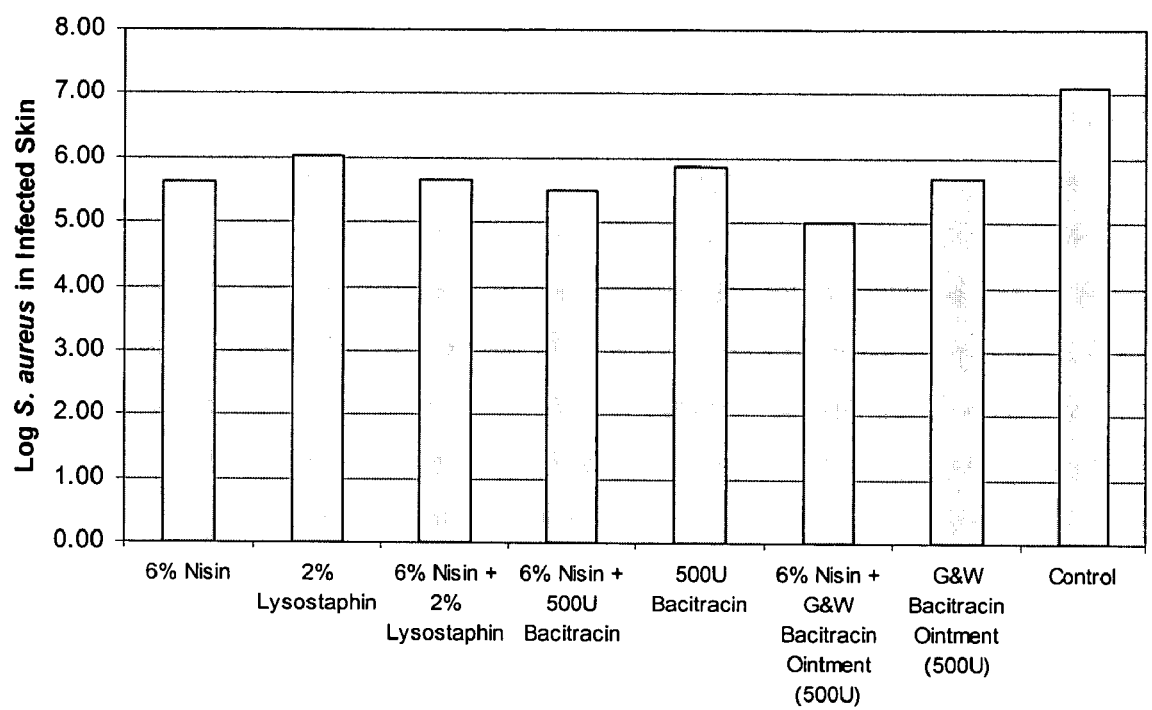
FIG. 2 shows the efficacy of nisin, lysostaphin, and bacitracin alone and in combination on S. aureus infection in abraded mouse skin using two different formulations of bacitracin.

For the following data, except where noted in FIG. 2, all antibiotic formulations were in a common polyethylene glycol (PEG) ointment (PEG 400 plus PEG 3350).

FIG. 1 shows that the efficacy of nisin alone increased with increasing nisin doses and decreases infectious CFUs by 2 logs, compared to a 3 log drop with mupirocin alone (on a molar bases, 2% mupirocin is twice the dose of 6% nisin). Neither drug alone was able to completely clear the infection. In contrast, 3 of 10 animals in the 2% nisin/2% mupirocin combination group and 5 of 11 in the 6% nisin/2% mupirocin combination group were cleared of infection and the infectious CFUs in the residual infections were reduced by 5 logs, 100-fold more than either therapy alone.

FIG. 2 shows the efficacy of nisin, lysostaphin, and bacitracin alone and in combination on S. aureus infection in abraded mouse skin using two different formulations of bacitracin: PEG ointment and a commercially available formulation from G&W Laboratories Inc (petrolatum base). None of these antibacterial agents administered independently, or administered in a composition comprising nisin, were significantly more efficacious than the independent administration of nisin (about 1.5 log reduction).

Figure 3:
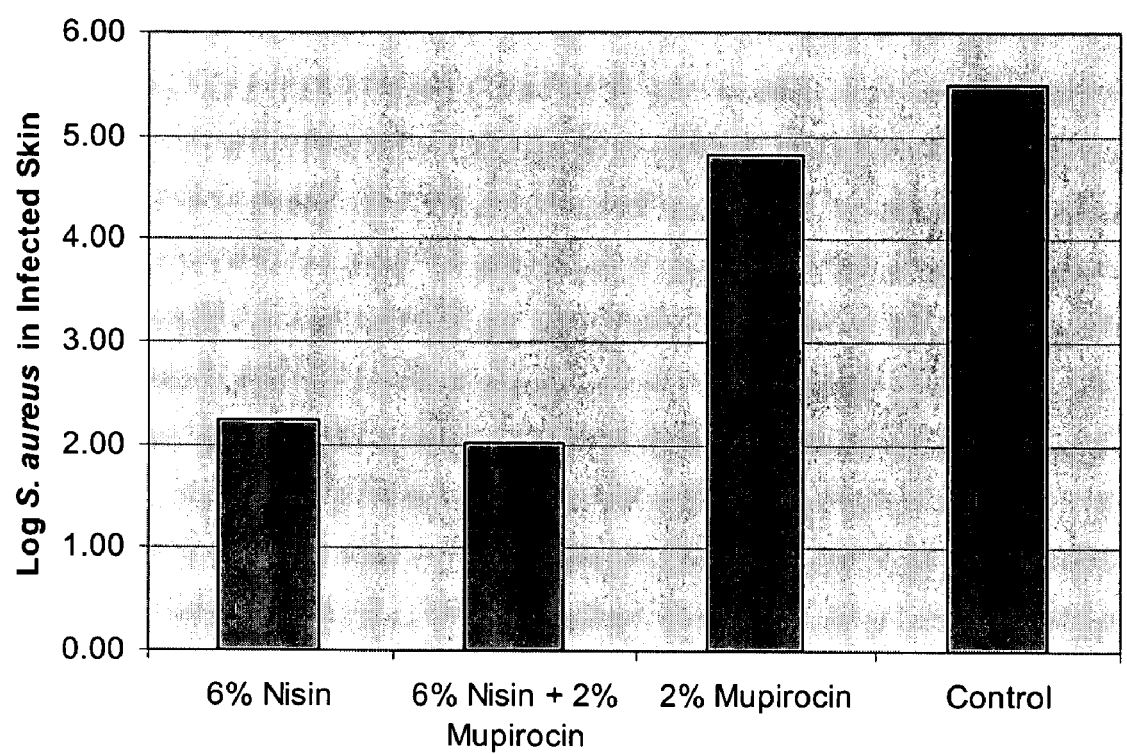
FIG. 3 shows the efficacy of nisin alone, mupirocin alone, and the combination of nisin and mupirocin on mupirocin-resistant S. aureus infection in abraded mouse skin.

As shown in FIG. 3, mupirocin exhibited minimal activity against an S. aureus strain resistant to mupirocin. However, nisin was capable of reducing infectious CFUs by 3 logs. Mupirocin has previously been shown to have poor activity against P. aeruginosa. However, nisin's spectrum of activity includes gram negative bacteria when formulated in the presence of chelators, surfactants, or essential oils.

Figure 4:
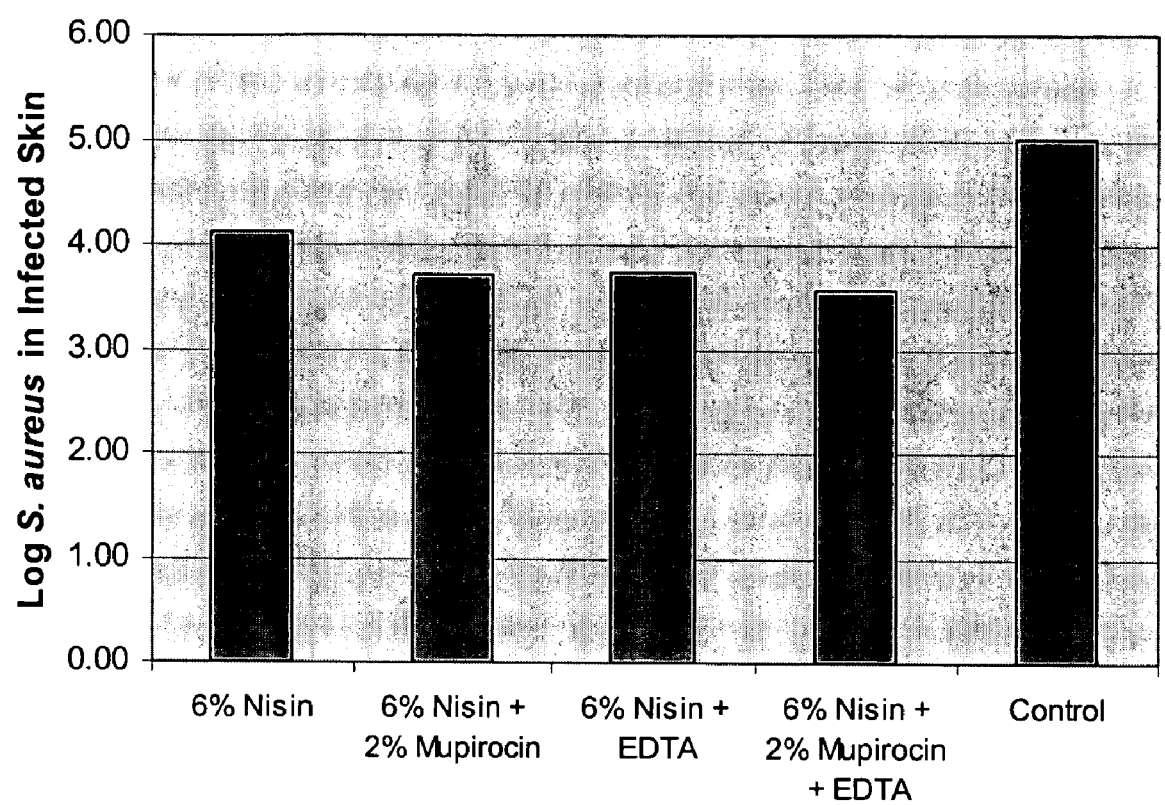
FIG. 4 shows the efficacy of nisin and mupirocin in combination with EDTA on P. aeruginosa infection in abraded mouse skin.

As shown in FIG. 4, nisin plus EDTA had more activity than nisin alone in this formulation and reduced infectious CFUs by 1.5 logs. Mupirocin does not add any additional activity to the nisin formulation.

Example 2

Compositions Comprising Mupirosin and Nisin Eliminate Inoculated Staphylococcus Aureus from Partial Thickness Wounds Experimental animals. A young female specific pathogen free (SPF: Looper Farms, North Carolina) pig weighing 25-30 kg was kept in house for two weeks prior to initiating the experiment. The animal was fed a basal diet ad libitum and housed individually in animal facilities (meeting American Association for Accreditation of Laboratory Animal standards) with controlled temperature (19-21° C.) and lights (12 h/12 h LD). The experimental animal protocols used for this study followed the federal guidelines for the care and use of laboratory animals (See U.S. Department of Health and Human Services, U.S. Department of Agriculture). Animals were monitored daily for any observable signs of pain or discomfort. In order to help minimize possible discomfort, an analgesic buprenorphine 0.03 mg/kg (Buprenex injectable; Reckitt Benckiser Hull, England) was given to each animal on the first day, and every third day thereafter, while under anesthesia; a fentanyl transdermal system: 25 µg/hr (Duragesic; Alza Corp. Mountain View, Calif.) were used during the entire experiment.

Animal Preparation, Wounding and Treatment. Each animal was anesthetized with Telazol HCl (1.4 mg/kg), Xylazine (2 mg/kg), Atropine (0.05 mg/kg) I.M. and inhalation of an isofluorane and oxygen combination. Hair on the back of the pig was clipped with standard animal clippers. Skin on both sides of the animal was prepared by washing with a non-antibiotic soap (NEUTROGENA) and sterile water. The animal was blotted dry with sterile gauze. Forty-eight partial thickness wounds measuring (10 mm×7 mm×0.3 mm deep) were made in the paravertebral and thoracic area of each animal with a specialized electrokeratome fitted with a 7 mm blade. The wounds were separated from one another by at least 7 cm of unwounded skin. Each wound was then inoculated with a known amount of *Staphylococcus aureus* ($10^6$ suspension). The suspension was lightly scrubbed into the test site for ten seconds using a sterile TEFLON spatula. After inoculation wounds were covered with TEGADERM polyurethane film dressing (3M, Inc.) for 24 hours before the initiation of the treatment in order to give the bacteria time to colonize the wounds and develop a biofilm.

Wound Inoculation. A fresh culture of pathogenic isolate obtained directly from American Type Culture Collection (ATCC), Rockville, Md., was used (*Staphylococcus aureus* ATCC #6538). The freeze-dried bacteria culture was recovered per ATCC standard recovering protocol. All inoculum suspensions were made by scraping the overnight growth from a culture plate into 4.5 ml of sterile water and making up the suspension until the turbidity of the suspension was equivalent to that of a McFarland #8 Turbidity Standard. This resulted in a suspension concentration of approximately $10^8$ colony forming units/ml (CFU/ml). The $10^8$ suspension was serially diluted to make an inoculum suspension with a concentration of $10^6$ CFU/ml in 35 mls of Tryptic Soy Broth (TSB). A small amount of the inoculum suspension was plated onto culture media to quantitate the exact concentration of viable organisms prior to the experiment. The inoculum suspension was used directly to inoculate each site. A 25 μl aliquot of the suspension was deposited into a sterile glass cylinder (22 mm diameter) in the center of each wound site. The suspension was lightly scrubbed into the test site for ten seconds using a sterile TEFLON spatula. After inoculation the wounds were covered with a polyurethane dressing for 48 hours to allow the bacteria to develop a biofilm on the wounds. Dressings were then removed to culture the baseline wounds and to treat the rest according to the experimental design described in FIG. 5. Wounds were treated twice per day.

Recovery Methods. Three wounds were cultured 48 hours post inoculation to quantitate the biofilm baseline, and two wounds from each treatment group on Days 2, 5 and 7 post treatment. At each sampling time, sites were cultured quantitatively. Each site was cultured only once. The wounded area was encompassed by a sterile glass cylinder (22 mm outside diameter) held in place by two handles. One mL of scrub solution was pipetted into the glass cylinder and the site was scrubbed with a sterile TEFLON spatula for 30 seconds.

Serial dilutions were made and scrub solutions were quantitated using the Spiral Plater System that deposits a small defined amount (50 μl) of suspension over the surface of a rotating agar plate. The selective media for *Staphylococcus aureus* was Mannitol Salt Agar. All samples were incubated aerobically for 24 hours at 37° C. After the incubation period (24 hrs), colonies on the plates were counted and the colony forming units per mL (CFU/ml) calculated. The presumptive identification test for the pathogen is the ability of *S. aureus* to coagulate rabbit plasma.

Three wounds per treatment group were cultured 2, 5 and 7 days post treatment. They were serially diluted, plated on Mannitol-salt agar, and incubated for 24 hours. After the incubation period colonies were counted and the Log colony forming units/mL determined. The geometric mean of the Log (CFU/mL) and standard deviation were calculated for each time and treatment. The initial inoculum size used for this experiment was 6.13 log cfu/ml. The baseline counts after 24 hours of inoculation in the wound environment were 7.48±1.0 log cfu/ml. The combined raw data for the total experiment is shown in FIG. 14. Active X is a composition having nisin (6%). Active Y is a composition having nisin (6%) and mupirocin (2%).

Figure 6:
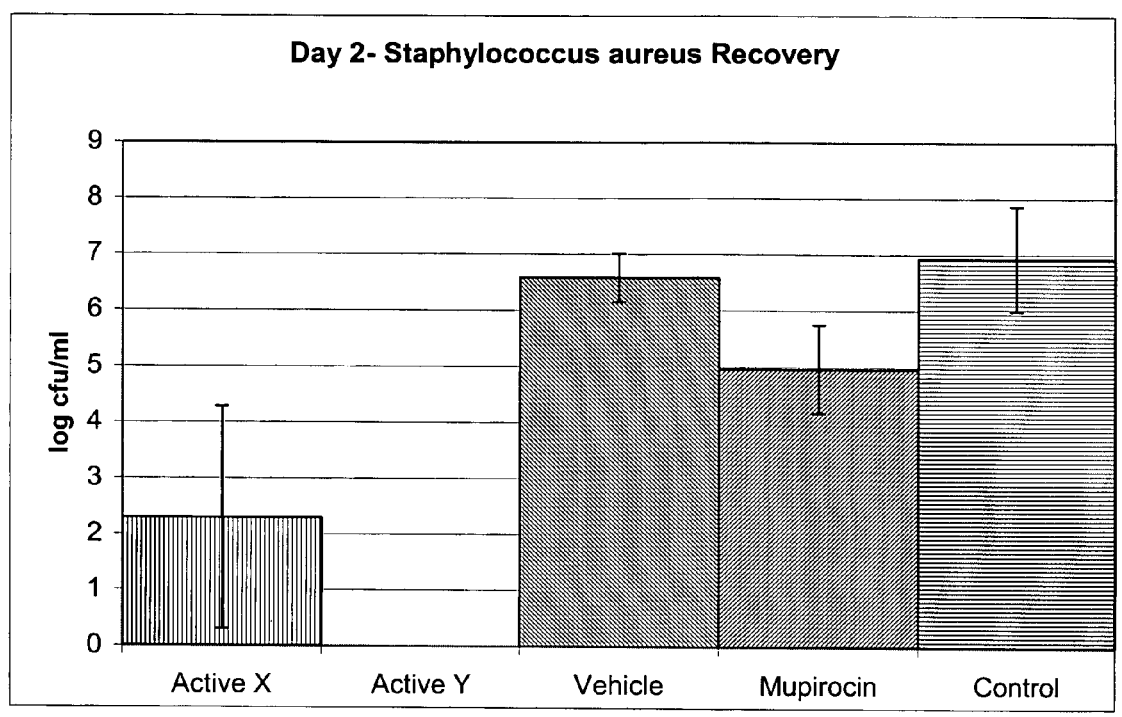
FIG. 6 shows Staphylococcus aureus growth in inoculated wounds two days after treatment with various agents.

The data comparing treatments day by day was as follows:

Two days after initial treatment of inoculated wounds, a composition comprising mupirocin and nisin was observed to completely eliminate *Staphylococcus aureus* from the wounds (See FIG. 6). The next most effective treatments were nisin, and mupirocin, which yielded 2.29±2.0 and 4.96±0.8 Log CFU/ml, respectively. The Vehicle-treated wounds and the wounds left air-exposed yielded similar numbers on this day (6.5 Log cfu/ml and 6.9 Log cfu/ml, respectively) (See FIG. 6).

Figure 7:
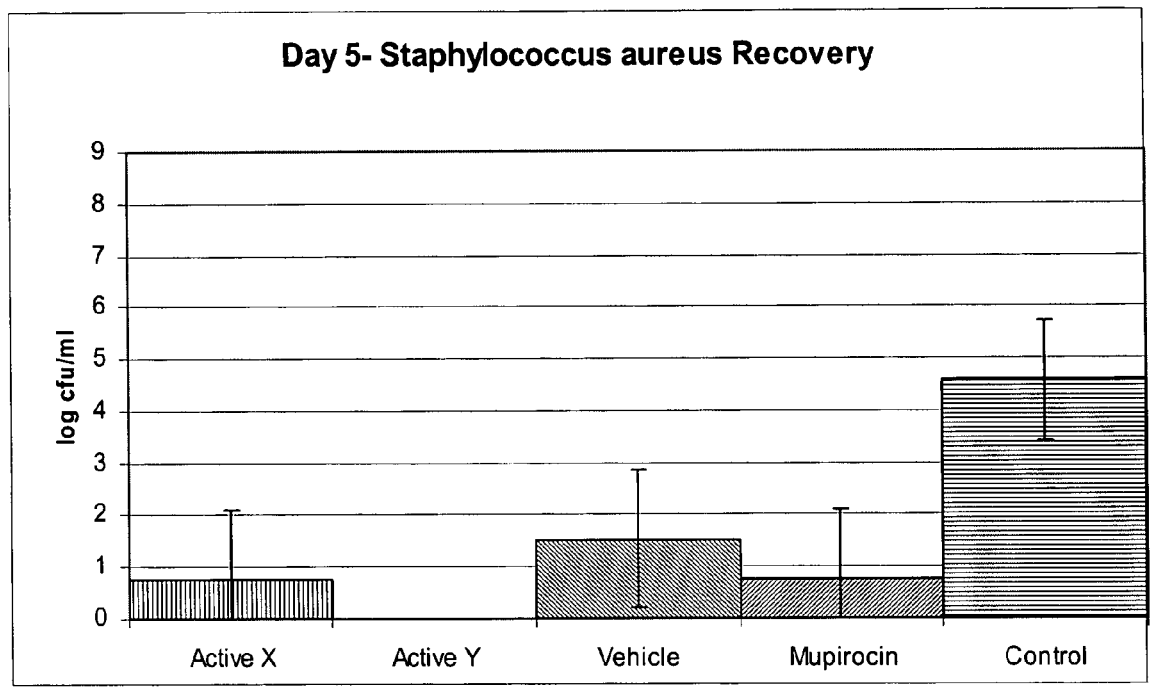
FIG. 7 shows Staphylococcus aureus growth in inoculated wounds five days after treatment with various agents.

On Day 5 after treatment, the same trend was observed as the prior assessment point. Bacteria cultured from wounds treated with a composition comprising mupirocin and nisin yielded no *Staphylococcus aureus* (See FIG. 7), with nisin being the next most effective treatment yielding a less than 1 Log cfu/ml. Mupirocin had a similar outcome. Vehicle-treated wounds yielded about 3 log cfu/ml of bacteria less than the negative control group, which had about 4.5 log cfu/ml bacteria (See FIG. 7).

Figure 8:
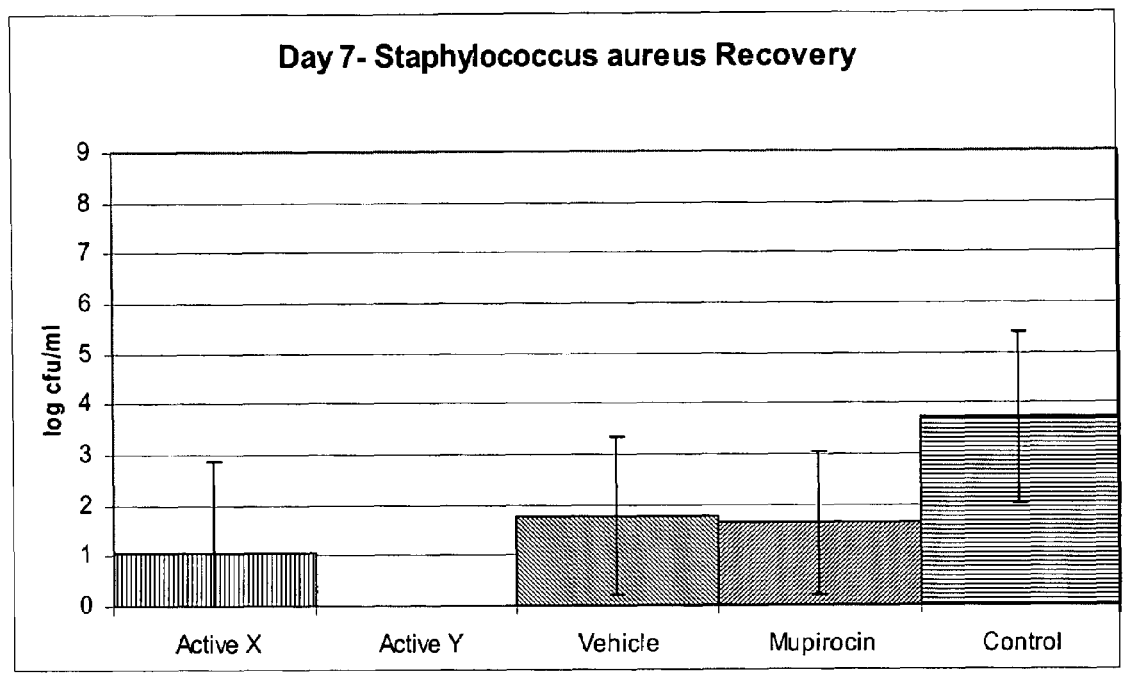
FIG. 8 shows Staphylococcus aureus growth in inoculated wounds seven days after treatment with various agents.
Figure 9:
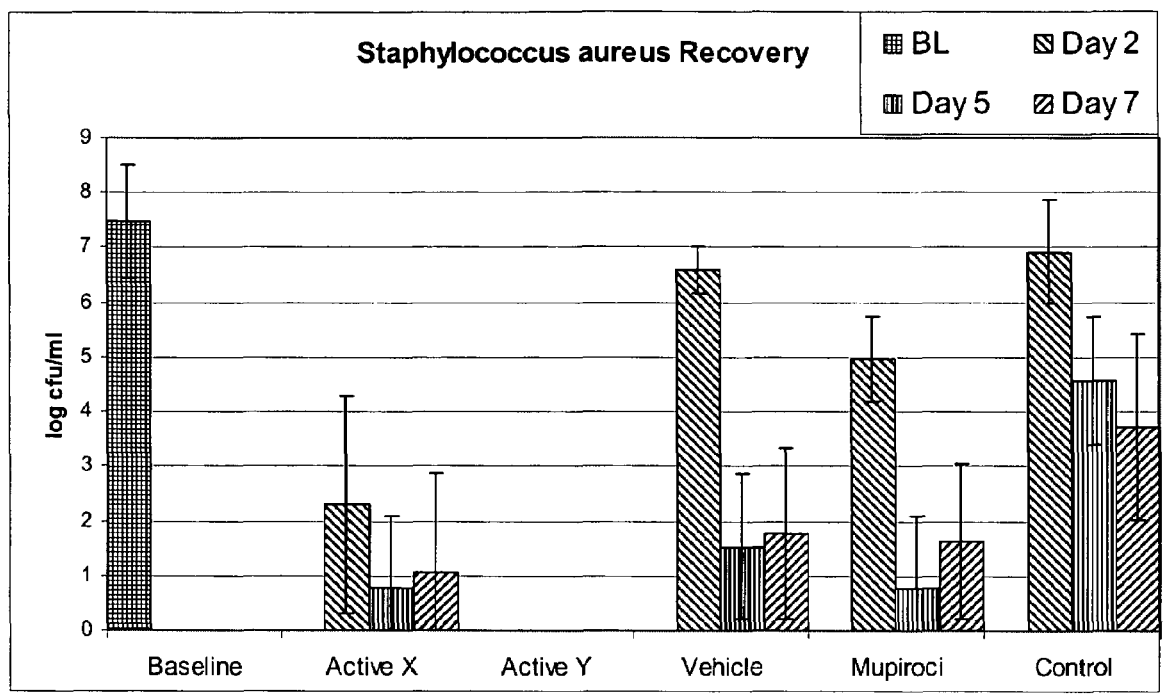
FIG. 9 shows a composite of Staphylococcus aureus growth in inoculated wounds two, five and seven days after treatment with various agents.

Day 7 post treatment, the final day of assessment, the trend observed in the previous two time points remained. Wounds treated with a composition comprising mupirocin and nisin yielded no *Staphylococcus aureus* (See FIG. 8), while nisin yielded 1.05±1.8 Log cfu/ml. Mupirocin yielded 1.63 Log cfu/ml, which was close to the Vehicle results (1.77±1.6 Log CFU/ml). The negative control resulted in a little less than 4 log cfu/ml (3.7) (See FIG. 8). A summary of the data from all three treatment timepoints is depicted in FIG. 9.

Example 3

Compositions Comprising Gentimycin and Nisin Eliminates *Staphylococcus aureus*

Mice provided a superficial skin abrasion and inoculated with *S. aureus* as described in Example 2 were treated with a composition comprising a combination of 6% nisin and 0.1% gentamicin. This combination eliminated substantially all detectable *S. aureus*.

Example 4

A Composition Comprising Nisin and Mupirocin is Superior to a Composition Comprising only Mupirocin in Treating Methicillin Sensitive and Methicillin Resistant *S. aureus*

Mice were provided a superficial skin abrasion as described in Example 2 and were infected with either methicillin sensitive *S. aureus* (MSSA) or methicillin resistant *S. aureus* (MRSA) and then treated with a composition comprising: vehicle (PEG cream) alone, mupirocin (2%), or mupirocin (2%) and nisin (6%) (Active Y). FIG. 10 shows the mean log (CFU/ml) of bacteria recovered after either a first or second treatment (MSSA) or after one and three days (MRSA). The combination of nisin and mupirocin was superior in treating (e.g., killing and/or inhibiting growth of) both MSSA and MRSA compared to controls and either treatment alone.

Example 5

Nisin does not Synergize with Mupirocin, Neomycin, or Gentamicin In vitro

In order to determine if nisin could function in a synergistic way with other antimicrobials to treat (e.g., kill and/or inhibit growth of) bacteria in vitro, the minimum inhibitory concentration (MIC) of nisin alone or nisin in combination with either mupirocin, neomycin or gentamicin were tested. The MIC was determined by calculating the log reduction of viable *S. aureus* following incubation with the amounts of nisin and other antimicrobials as indicated in FIG. 11.

As documented in FIG. 11, none of the antimicrobials tested (i.e., mupirocin, neomycin, and gentamicin) displayed the ability to synergize in vitro with nisin.

Example 6

Nisin does not Synergize with Neomycin or Gallidermin in Treating Skin Infection In order to determine if nisin could function in a synergistic way with other antimicrobials to treat (e.g., kill and/or inhibit growth of) bacteria in a superficial wound model (See Example 2), nisin was used in combination with either neomycin or gallidermin and tested. Nisin did not synergize with neomycin nor with gallidermin in the skin infection model.

Example 7

Nisin does synergize with Gentamicin and Gallidermin does Synergize with Mupirocin in Treating Skin Infection In order to determine if nisin or gallidermin could function in a synergistic way with other antimicrobials to treat (e.g., kill and/or inhibit growth of) bacteria in a superficial wound model (See Example 2), nisin or gallidermin were used in combination with either gentamicin and mupirocin, respectively, and tested. Nisin did synergize with gentamicin and gallidermin did synergize with mupirocin to reduce bacterial counts in the skin infection model.

Example 8

Mupirocin does not Synergize with Bacitracin in Treating Skin Infection

Figure 12:
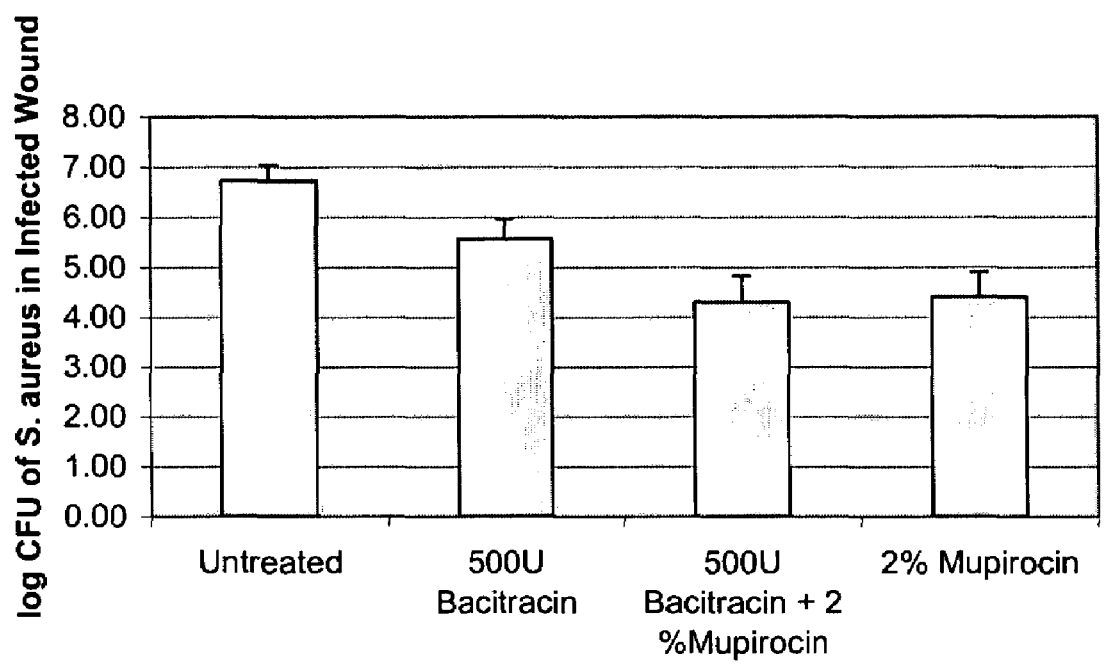
FIG. 12 shows that mupirocin does not synergize with or provide additive benefit together with bacitracin in treating skin infection.

In order to determine if mupirocin could function in a synergistic way with bacitracin to treat (e.g., kill and/or inhibit growth of) bacteria in a superficial wound model (See Example 2), mupirocin was used in combination with bacitracin and tested for the ability to treat bacteria. As shown in FIG. 12, mupirocin did not synergize with bacitracin, nor was there an additive benefit when the two were used together in the reduction of *S. aureus* in the infected wound model.

Example 9

Figure 13:
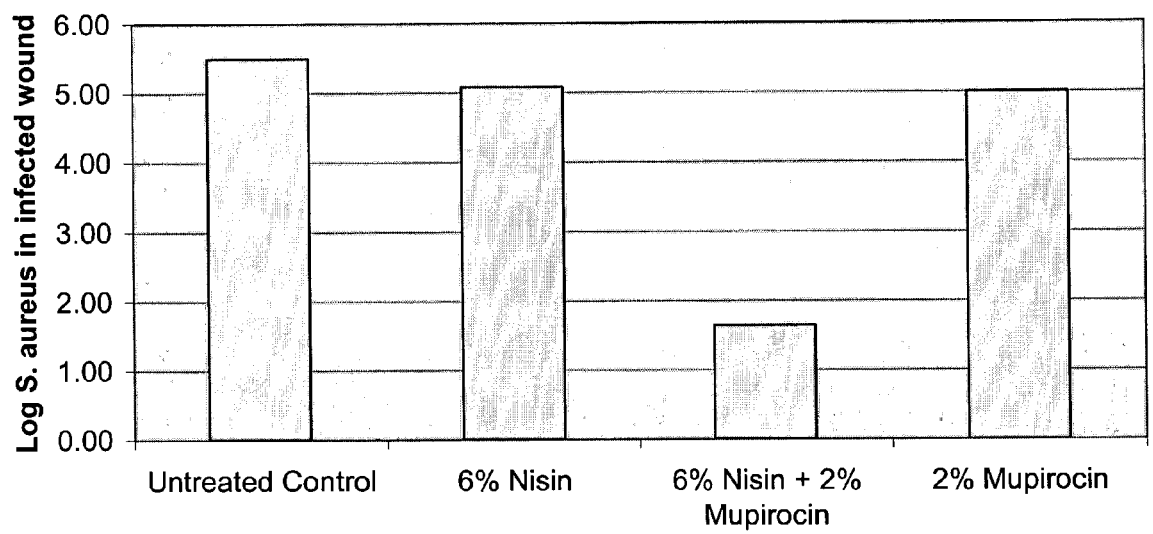
FIG. 13 shows that nisin and mupirocin function synergistically to treat S. aureus in a suture infection mouse model.

A Composition comprising Nisin and Mupirocin Provide a Synergistic Ability to Treat *S. aureus* in a Suture Infection Model It was determined whether nisin and mupirocin, either alone or in combination with each other, would be able to treat *S. aureus* in a deep tissue infection model. A suture skin infection model was generated in which a deep cut (e.g., one needing sutures to close) was made in a mouse and *S. aureus* introduced into the incision. As shown in FIG. 13, nisin and mupirocin alone show very little efficacy in treating the *S. aureus*. However, the combination of nisin plus mupirocin nearly eradicated the infection. Thus, a combination of nisin and mupirocin can be used to treat a deep tissue infection as well as a subcutaneous infection.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A method of killing and/or inhibiting growth of bacteria comprising administrating to said bacteria a topical ointment comprising nisin and mupirocin, wherein said ointment contains polyethylene glycol (PEG) 400, PEG 3350, 6% nisin and 2% mupirocin, and wherein said bacteria is *Staphylococcus aureus*.

2. The method of claim 1, wherein said bacteria are pathogenic bacteria.

3. The method of claim 1, wherein said *Staphylococcus aureus* are antibiotic resistant.

4. The method of claim 3, wherein said *Staphylococcus aureus* are methicillin resistant.

5. A method for treating or preventing infection comprising exposing a surface of a subject in need thereof to a topical pharmaceutical formulation containing polyethylene glycol (PEG) 400, PEG 3350, 6% nisin and 2% mupirocin, wherein said infection is caused by *Staphylococcus aureus*.

6. The method of claim 5, wherein growth of *Staphylococcus aureus* on said surface is inhibited or prevented.

7. The method of claim 5, wherein said surface comprises a wound surface.

8. The method of claim 5, wherein said surface comprises a skin surface.

9. The method of claim 5, wherein said subject is a human.

10. The method of claim 5, wherein said exposing results in a 3 log or greater reduction in bacteria responsible for said infection.

11. The method of claim 5, wherein said exposing results in a lack of detectable bacteria responsible for said infection.

12. The method of claim 10, wherein said reduction occurs within three days of said treating.

13. The method of claim 10, wherein said reduction occurs with two days of said treating.

14. A method of killing and/or inhibiting growth of bacteria comprising administrating to said bacteria a topical ointment comprising nisin and mupirocin, wherein said ointment contains polyethylene glycol (PEG) 400, PEG 3350, 6% nisin and 2% mupirocin, and wherein said administering produces a 3 log or more reduction in viable bacteria, and wherein said bacteria is *Staphylococcus aureus*.

15. The method of claim 14, wherein said bacteria are present on skin.

16. The method of claim 14, wherein said bacteria are present within a wound.

17. The method of claim 1, wherein said administrating results in a more than additive killing and/or growth inhibition of said bacterial cells compared to administration of nisin or mupirocin alone.

18. The method of claim 5, wherein said exposing results in a more than additive killing and/or growth inhibition of said bacterial cells compared to administration of nisin or mupirocin alone.

19. The method of claim 13, wherein said administrating results in a more than additive killing and/or growth inhibition of said bacterial cells compared to administration of nisin or mupirocin alone.

* * * * *